US011306130B2

(12) United States Patent
Vagner et al.

(10) Patent No.: US 11,306,130 B2
(45) Date of Patent: Apr. 19, 2022

(54) PAR3 MIMETIC PEPTIDES AND USES THEREOF

(71) Applicants: ARIZONA BOARD OF REGENTS ON BEHALF OF THE UNIVERSITY OF ARIZONA, Tucson, AZ (US); BOARD OF REGENTS, THE UNIVERSITY OF TEXAS SYSTEM, Austin, TX (US)

(72) Inventors: Josef Vagner, Tucson, AZ (US); Scott A. Boitano, Tucson, AZ (US); Theodore J. Price, Austin, TX (US); Gregory O. Dussor, Austin, TX (US)

(73) Assignees: ARIZONA BOARD OF REGENTS ON BEHALF OF THE UNIVERSITY OF ARIZONA, Tucson, AZ (US); BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 300 days.

(21) Appl. No.: 16/090,526

(22) PCT Filed: Mar. 31, 2017

(86) PCT No.: PCT/US2017/025508
§ 371 (c)(1),
(2) Date: Oct. 1, 2018

(87) PCT Pub. No.: WO2017/173346
PCT Pub. Date: Oct. 5, 2017

(65) Prior Publication Data
US 2019/0119349 A1 Apr. 25, 2019

Related U.S. Application Data (60) Provisional application No. 62/317,309, filed on Apr. 1, 2016.

(51) Int. Cl.
| | |
|---|---|
| *C07K 14/705* | (2006.01) |
| *C07K 5/083* | (2006.01) |
| *A61K 47/60* | (2017.01) |
| *A61K 47/62* | (2017.01) |
| *C07K 7/06* | (2006.01) |
| *A61K 47/54* | (2017.01) |
| *A61K 47/61* | (2017.01) |
| *C07K 7/08* | (2006.01) |
| *A61P 25/00* | (2006.01) |

(52) U.S. Cl.
CPC .......... *C07K 14/705* (2013.01); *A61K 47/542* (2017.08); *A61K 47/543* (2017.08); *A61K 47/60* (2017.08); *A61K 47/61* (2017.08); *A61K 47/62* (2017.08); *A61P 25/00* (2018.01); *C07K 5/081* (2013.01); *C07K 7/06* (2013.01); *C07K 7/08* (2013.01); *C07K 2319/03* (2013.01)

(58) Field of Classification Search
CPC ........ C07K 14/705; C07K 7/08; C07K 5/081; C07K 7/06; C07K 2319/03; A61K 47/542; A61K 47/60; A61K 47/61; A61K 47/62; A61K 47/543; A61P 25/00
See application file for complete search history.

(56) References Cited

U.S. PATENT DOCUMENTS

| | | | |
|---|---|---|---|
| 3,989,816 A | 11/1976 | Rajadhyaksha | |
| 4,444,762 A | 4/1984 | Rajadhyaksha | |
| 7,176,283 B1 | 2/2007 | Coughlin et al. | |
| 2007/0179090 A1* | 8/2007 | Kuliopulos | .......... C07K 14/723 435/69.1 |
| 2009/0297576 A1 | 12/2009 | Yamit et al. | |
| 2013/0072420 A1 | 3/2013 | Skerra et al. | |

FOREIGN PATENT DOCUMENTS

WO  2016/049355  3/2016

OTHER PUBLICATIONS

Heuberger et al, Protease-activated receptors (PARs): mechanisms of action and potential therapeutic modulators in PAR-driven inflammatory diseases, Thrombosis Journal, 2019, 17, pp. 1-24.*
Hansen et al, Tethered ligand-derived peptides of proteinase-activated receptor 3 (PAR3) activate PAR1 and PAR2 in Jurkat T cells, Immunology, 2004, 112, pp. 183-190.*
Drumm et al, Genetic Variation and Clinical Heterogeneity in Cystic Fibrosis, Annu. Rev. Pathol. Mech. Dis., 2012, 7, pp. 267-282.*
Yampolsk et al, The Exchangeability of Amino Acids in Proteins, Genetics, 2005, 170, pp. 1459-1472.*
Supplemental Data of Stavenuiter et al. (Blood, 2014, 124, pp. 3480-3489, filed with IDS), pp. 1-12.*
Ostrowska et al, PAR-2 activation and LPS synergistically enhance inflammatory signaling in airway epithelial cells by raising PAR expression level and interleukin-8 release, Am J Physiol Lung Cell Mol Physiol, 2007, 293, pp. L1208-L1218.*
Alleti, R et al. Synthesis and Characterization of Time-resolved Fluorescence Probes for Evaluation of Competitive Binding Melanocortin Receptors. Bioorganic and Medicinal Chemistry. Jul. 2, 2013, vol. 21, No. 17, pp. 1-21.
Boitano, S. et al. Developmental and Evaluation of Small Peptidomimetic Ligands to Protease-Activated Receptor-2 (PAR2) through the Use of Lipid Tethering. Plos ONE Jun. 13, 2014; vol. 9, No. 6; pp. 1-16.
Hart, NJ et al. Heterobivalent GLP-1/Glibenclamide for Targeting Pancreatic B-cells. Chembiochem. Nov. 20, 2013; vol. 15, No. 1, pp. 135-145.
International Search Report & Written Opinion, International Patent Application No. PCT/US2017/025508, dated Aug. 7, 2017.

(Continued)

*Primary Examiner* — Li N Komatsu
(74) *Attorney, Agent, or Firm* — Casimir Jones, S.C.; Robert A. Goetz (57) ABSTRACT

This invention is in the field of medicinal pharmacology. In particular, the invention relates to protease activated receptor type 3 (PAR3) modulating compounds (e.g., mimetic peptides), compositions comprising such modulating compounds, and their use as therapeutics for the treatment of conditions involving PAR3 activity.

8 Claims, 7 Drawing Sheets
Specification includes a Sequence Listing.

(56) References Cited

OTHER PUBLICATIONS

Laskin, DL et al. Chemotactic Activity of Collagen-Like Polypeptides for Human Peripheral Blood Neutrophils. Journal of Leukocyte Biology. Mar. 1986; vol. 39, No. 3p pp. 255-266.
Myrberg, H. et al. Design of a Tumor-Homing Cell-Penetrating Peptide. Bioconjugate Chemistry. Nov. 15, 2007; vol. 19, No. 1; pp. 70-75.
Odell, D. et al. Influence of Membrane Anchoring and Cytoplasmic Domains on the Fusogenic Activity of Vesicular Stomatitis Virus Glycoprotein G. Journal of Virology. Oct. 1997; vol. 71, No. 10; pp. 7996-8000.
Stavenuiter, F. et al. Noncanonical PAR3 Activation by Factor Xa Identifies a Novel Pathway for Tie2 Activation and Stabilization of Vascular Integrity. Blood. Oct. 15, 2014; vol. 124, No. 23; pp. 3480-3489.

\* cited by examiner

Protease Activated Receptor Gene Family mRNA Expression Across Tissues

FIG. 3

From linnarssonlab.org/drg
Unbiased classification of sensory neuron types by large-scale single-cell RNA sequencing
(Published in Nature Neuroscience)

Dmitry Usoskin[1], Alessandro Furlan[1], Saiful Islam[1], Hind Abdo[1], Peter Lönnerberg[1], Daohua Lou[1], Jens Hjerling-Leffler[1], Jesper Haeggström[2], Olga Kharchenko[1], Peter Kharchenko[3,4], Sten Linnarsson[1] and Patrik Ernfors[1]

[1] Division of Molecular Neurobiology,
[2] Division of Physiological Chemistry, Karolinska Institutet
[3] Center for Biomedical Informatics, Harvard Medical School
[4] Division of Hematology/Oncology, Children's Hospital NF = large diameter neurofilament positive
NP = non-peptidergic
PEP = peptidergic
TH = tyrosine hydroxylase positive

PAR3 MIMETIC PEPTIDES AND USES THEREOF

CROSS-REFERENCE TO RELATED APPLICATIONS

The present application is a U.S. 371 national phase entry of International Patent Application No. PCT/US2017/025508, filed Mar. 31, 2017, which claims priority to U.S. Provisional Patent Application Ser. No. 62/317,309, filed Apr. 1, 2016, the disclosure of which is herein incorporated by reference in their entireties.

STATEMENT REGARDING FEDERALLY SPONSORED RESEARCH OR DEVELOPMENT

This invention was made with government support under Grant Nos. R01 NS073664 and R56 NS098826 awarded by NIH. The government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 2,000 Byte ASCII (Text) file named "34821-252_ST25," created on Feb. 12, 2021.

FIELD OF THE INVENTION

This invention is in the field of medicinal pharmacology. In particular, the invention relates to protease activated receptor type 3 (PAR$_3$) modulating compounds (e.g., mimetic peptides), compositions comprising such modulating compounds, and their use as therapeutics for the treatment of conditions involving PAR$_3$ activity.

INTRODUCTION

Chronic pain is a neurological disorder that impacts the lives of millions of Americans. Current treatments for chronic pain are limited by abuse potential and intolerable side effects.

Accordingly, improved methods for pain are needed.

SUMMARY OF THE INVENTION

The dorsal root ganglion (DRG) contains sensory neurons that innervate the surface of the body and many visceral organs. Included amongst these neurons are nociceptors, specialized neurons that detect damaging or potentially damaging stimuli, which are required for the detection of acute pain and play a key role in the development and maintenance of chronic pain states. RNA-seq has recently been used to elucidate the transcriptome of this tissue in mouse and rat but the transcriptome of human DRG has not been explored.

Experiments conducted during the course of developing embodiments for the present invention identified the conspicuous DRG enriched gene F2RL2 which encodes PAR$_3$. Such experiments further demonstrated that several novel PAR$_3$ mimetic peptides robustly activated calcium signaling in trigeminal ganglion neurons and caused mechanical hypersensitivity after hindpaw injection in mice. Such experiments concluded PAR$_3$ to be a novel pain target.

Accordingly, the present invention relates to modulating compounds which function as activators and inhibitors of PAR$_3$ proteins. The invention further relates to methods of treating, ameliorating, or preventing disorders in a patient, such as those that are responsive to either PAR$_3$ activation or PAR$_3$ inhibition, comprising administering to a subject (e.g., a human patient) a composition comprising one or more of the PAR$_3$ modulating compounds of the invention and, potentially, additional agent(s). Such disorders include those characterized by aberrant PAR$_3$ activity (e.g., chronic pain).

The present invention is not limited to particular types or kinds of modulating compounds which function as activators and inhibitors of PAR$_3$ activity. In some embodiments, the modulating compounds include small molecule compounds and mimetic peptides.

In certain embodiments, the modulating compounds which function as activators and inhibitors of PAR$_3$ proteins are PAR$_3$ mimetic peptides. For example, in certain embodiments, the present invention provides compositions comprising a PAR$_3$ mimetic peptide. In some embodiments, the PAR$_3$ mimetic peptide is encompassed within Formula I:

[activating peptide sequence]-[linker moiety]-[cell-membrane anchoring moiety], including pharmaceutically acceptable salts, lipidated analogs, pegylated analogs, and/or prodrugs thereof.

Such PAR$_3$ mimetic peptides are not limited to a particular activating peptide sequence. In some embodiments, the peptide sequence comprises two or more contiguous amino acid residues. In some embodiments, the two or more contiguous amino acid residues render the resulting PAR$_3$ mimetic peptide as a PAR$_3$ activator and/or a PAR$_3$ inhibitor. In some embodiments, the amino acid sequence is selected from the group consisting of TFRGAPPNSFEEF (SEQ ID NO:1), GAPPNSFEEF (SEQ ID NO:2), TRFGAP (SEQ ID NO:3), and TFR.

Such PAR$_3$ mimetic peptides are not limited to a particular position for the activating peptide sequence. In some embodiments, the activating peptide sequence is positioned at the N-terminus of the PAR$_3$ mimetic peptide.

Such PAR$_3$ mimetic peptides are not limited to a particular linker moiety. In some embodiments, the linker moiety comprises a chemical moiety configured to bridge the activating peptide sequence and cell-membrane anchoring moiety. In some embodiments, the linker moiety comprises a chemical moiety selected from the group consisting of a substituted aliphatic chain, an unsubstituted aliphatic chain, substituted aromatic moiety, an unsubstituted aromatic moiety, a linear polymer, one or more polyethylene glycol (PEG) moieties, one or more 3,19-dioxo-2,8,11,14,21-pentaoxa-4,18-diazatricosan-23-oic acid residue derivative moieties, and/or any combination thereof. In some embodiments, the linker moiety comprises a polyethylene glycol (PEG) moiety. In some embodiments, the linker moiety comprises multimers of 3,19-dioxo-2,8,11,14,21-pentaoxa-4,18-diazatricosan-23-oic acid. In some embodiments, the linker moiety comprises a polyethylene glycol (PEG) moiety. In some embodiments, the linker moiety is a linear polymer comprising monomeric subunits. In some embodiments, the linear polymer comprises saccharide moieties, peptide moieties, lactone moieties, acrylate moieties, and/or synthetic polymer moieties. In some embodiments, the linear polymer comprises collagen-like polypeptides and/or synthetic surrogates of spider silk.

Such PAR$_3$ mimetic peptides are not limited to a particular cell-membrane anchoring moiety. In some embodiments, the cell-membrane anchoring moiety comprises a hydrophobic chemical moiety or a synthetic structure that forms a non-covalent binding interaction with a cell membrane.

Such $PAR_3$ mimetic peptides are not limited to a particular position for the cell-membrane anchoring moiety. In some embodiments, the cell-membrane anchoring moiety is positioned at the C-terminus of the $PAR_3$ mimetic peptide. In some embodiments, the cell-membrane anchoring moiety comprises a lipid moiety. In some embodiments, the cell-membrane anchoring moiety comprises a saturated or unsaturated hydrocarbon moiety. In some embodiments, the cell-membrane anchoring moiety is hexadecyl. In some embodiments, the cell-membrane anchoring moiety is a saturated $C_{12}$-$C_{20}$ alkyl residue. In some embodiments, the cell-membrane anchoring moiety is a cell-membrane homing structure. In some embodiments, the cell-membrane anchoring moiety is a cell-penetrating moiety. In some embodiments, the cell-membrane anchoring moiety is a transmembrane domain.

In some embodiments, the $PAR_3$ mimetic peptide is configured to modulate $PAR_3$ biological activity. For example, in some embodiments, the $PAR_3$ mimetic peptide is configured to activate $PAR_3$ biological activity. In some embodiments, the $PAR_3$ mimetic peptide is configured to antagonize $PAR_3$ biological activity.

In certain embodiments, the present invention provides methods for modulating the activity of $PAR_3$ in a subject (e.g., human subject) (e.g., non-human subject), comprising administering to the subject a $PAR_3$ modulating compound as described herein (e.g., a mimetic peptide) of the present invention. In some embodiments, the subject is experiencing aberrant $PAR_3$ activity. In some embodiments, the subject is at risk for experiencing aberrant $PAR_3$ activity. In some embodiments, the subject has or is at risk for developing chronic pain involving aberrant $PAR_3$ activity.

In some embodiments, the methods further comprise administering to the subject one or more anti-pain related agents.

In certain embodiments, the pharmaceutical composition comprises a $PAR_3$ mimetic peptide of the present invention and a pharmaceutically acceptable carrier.

In certain embodiments, the present invention provides kits comprising a pharmaceutical composition comprising a $PAR_3$ mimetic peptide of the present invention.

DETAILED DESCRIPTION OF THE INVENTION

Figure 1:
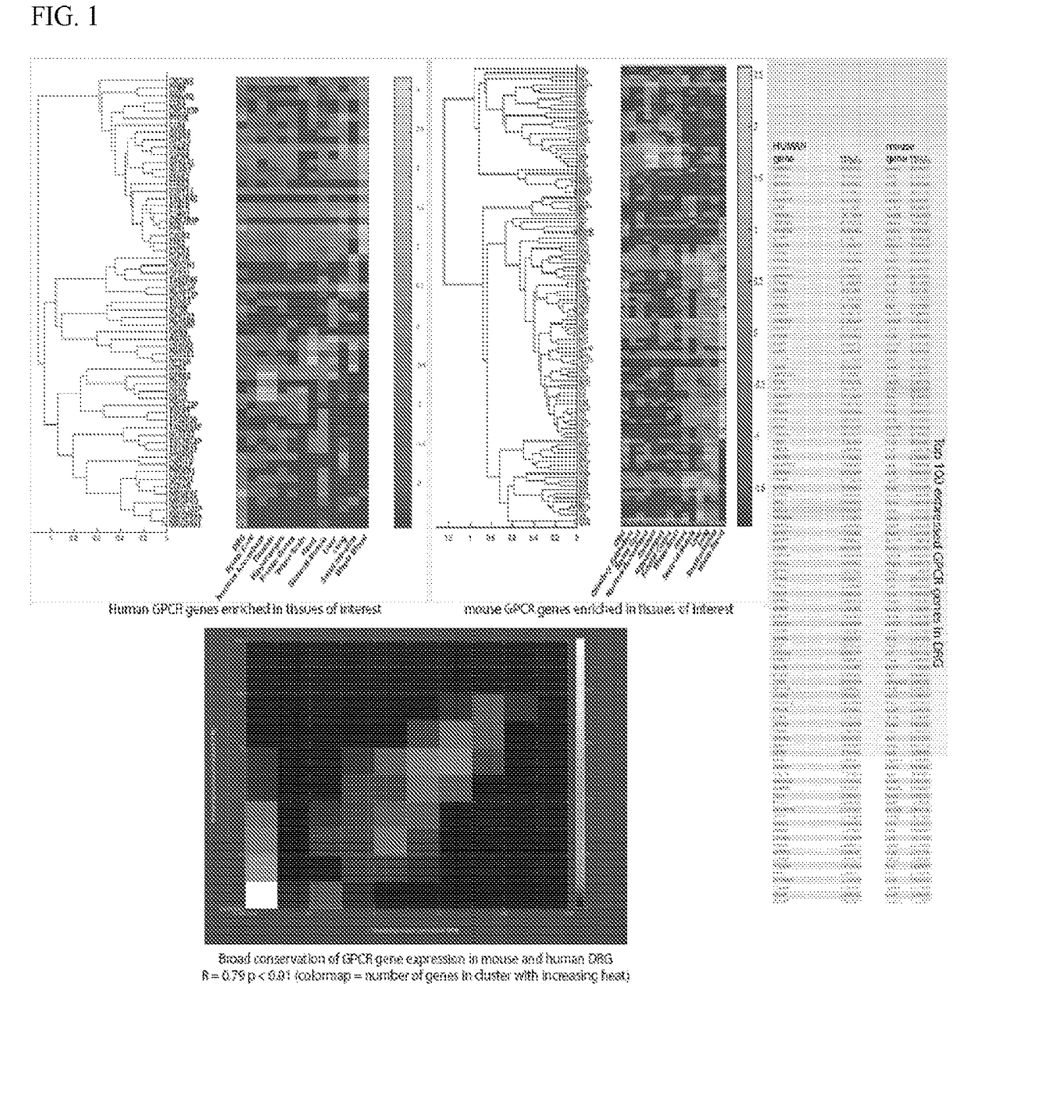
FIG. 1 shows human and mouse GPCR genes enriched in tissues of interest.
Figure 2:
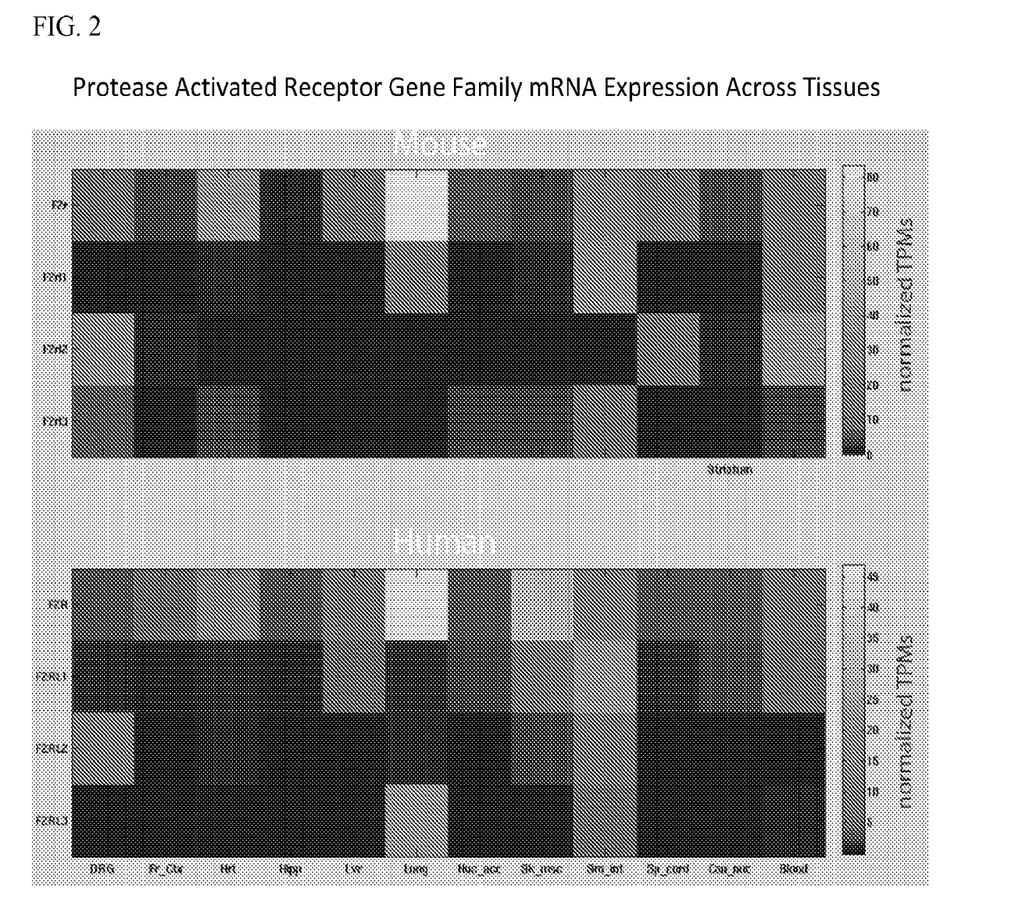
FIG. 2 shows protease activated receptor gene family mRNA expression across tissues.
Figure 3:
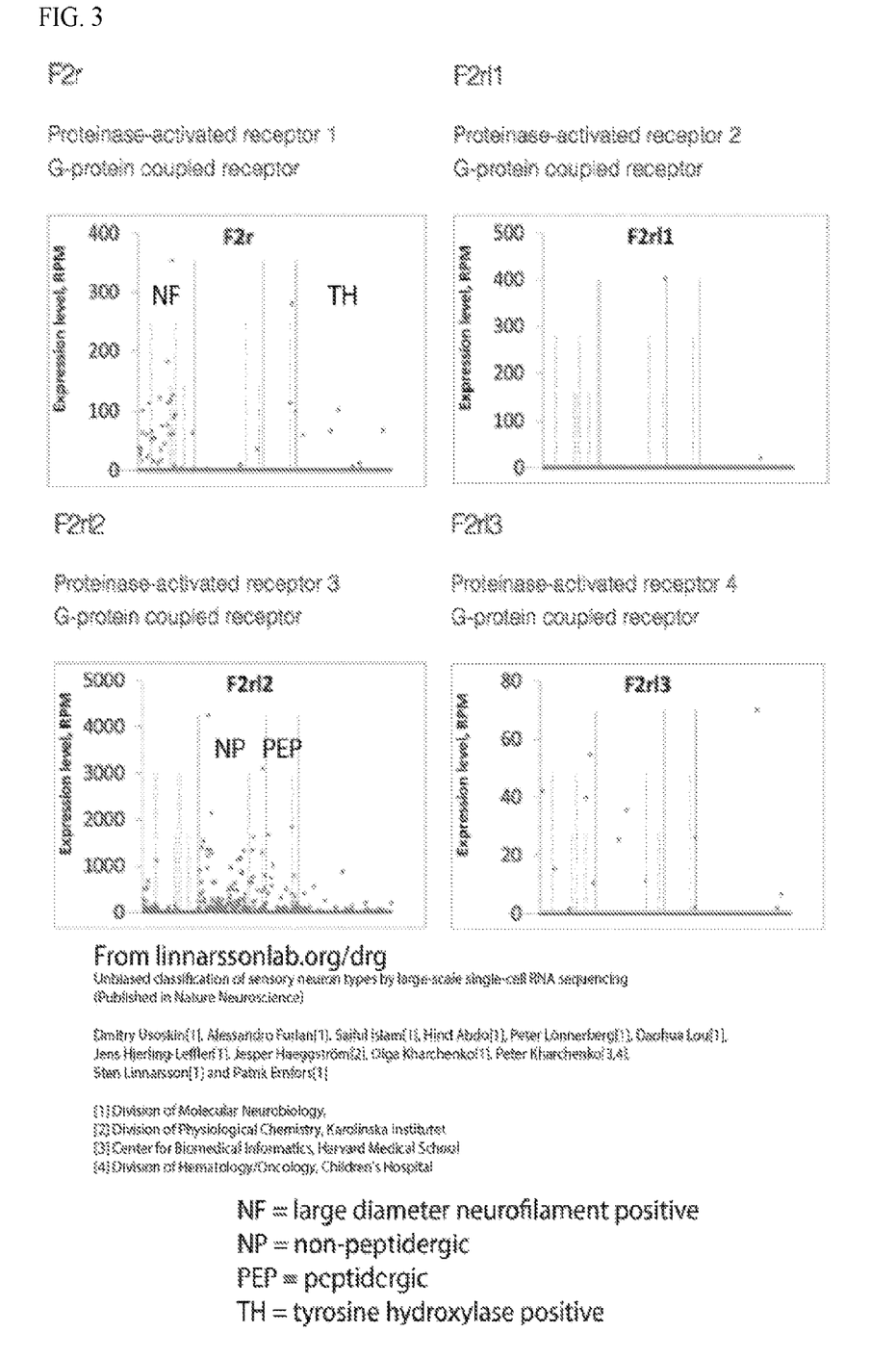
FIG. 3 shows RNA-seq-based cell expression for PAR family receptors in mouse DRG.
Figure 4:
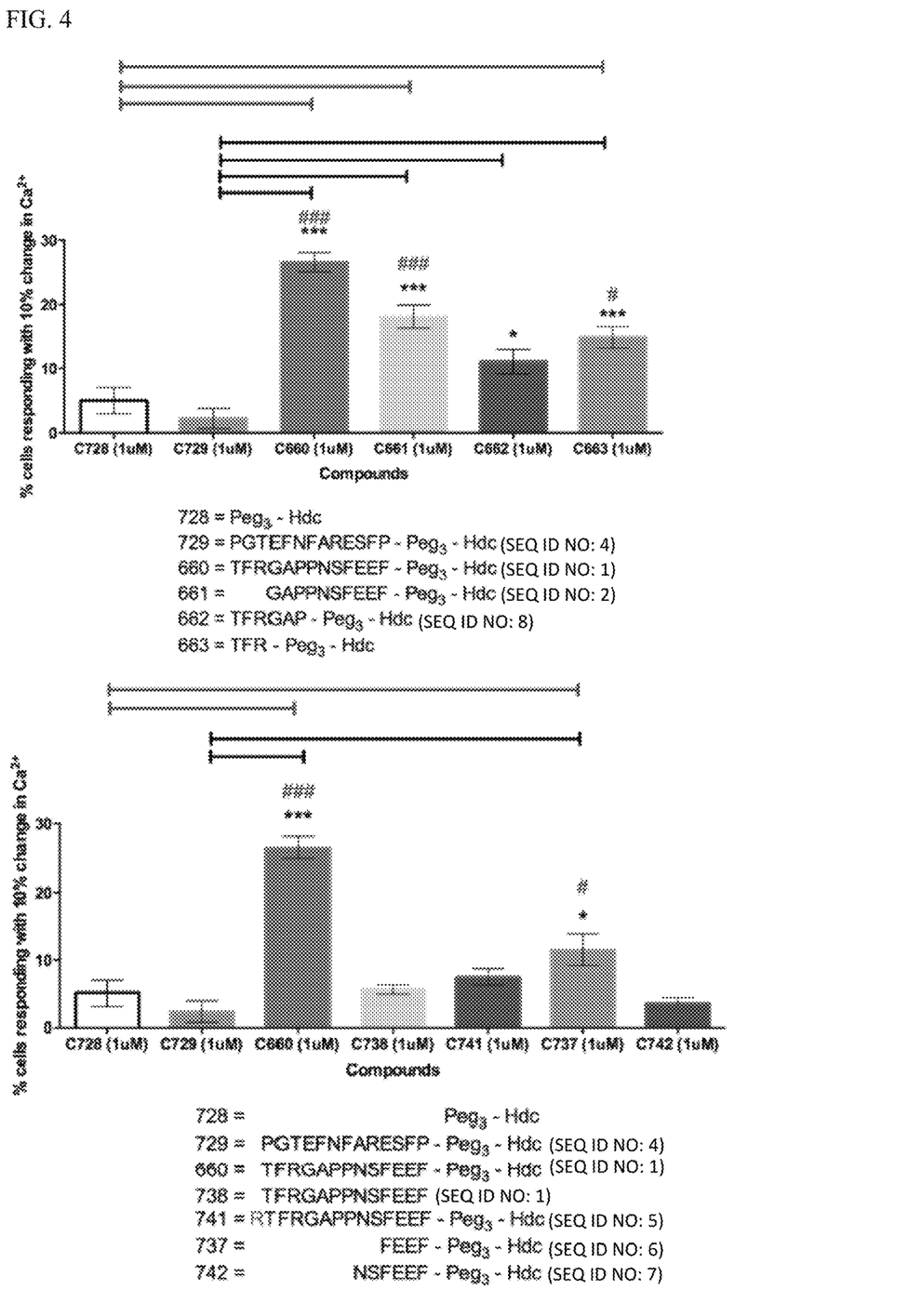
FIG. 4 shows calcium imaging in trigeminal ganglion neurons from mice revealing that a PAR3-directed synthetic tethered ligand induces calcium influx.
Figure 5:
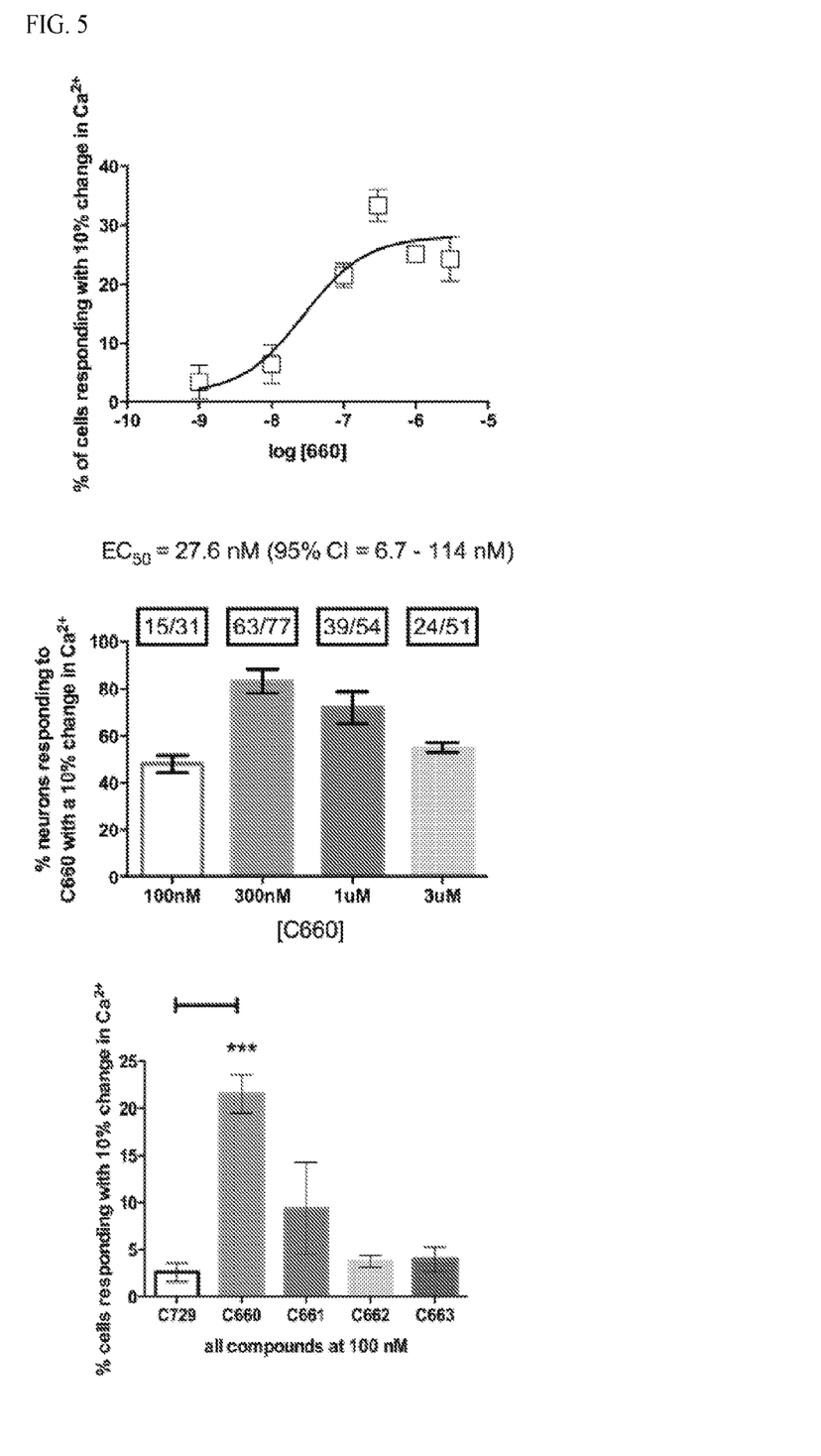
FIG. 5 shows that Compound 660 is a putative $PAR_3$ agonist with an effect largely upon neurons.
Figure 6:
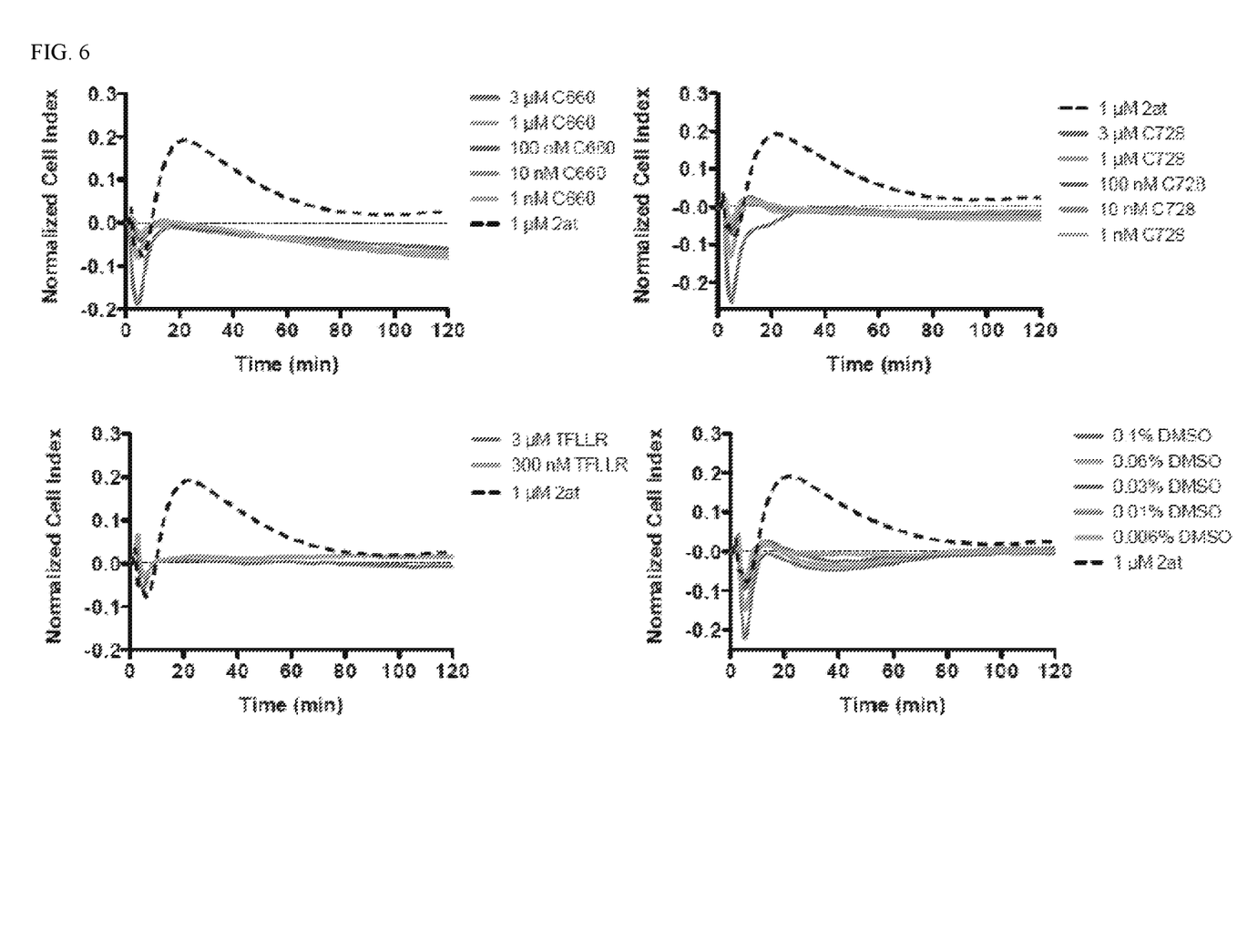
FIG. 6 shows that Compound 660 is devoid of action on $PAR_2$ expressing 16-HBE cells.
Figure 7:
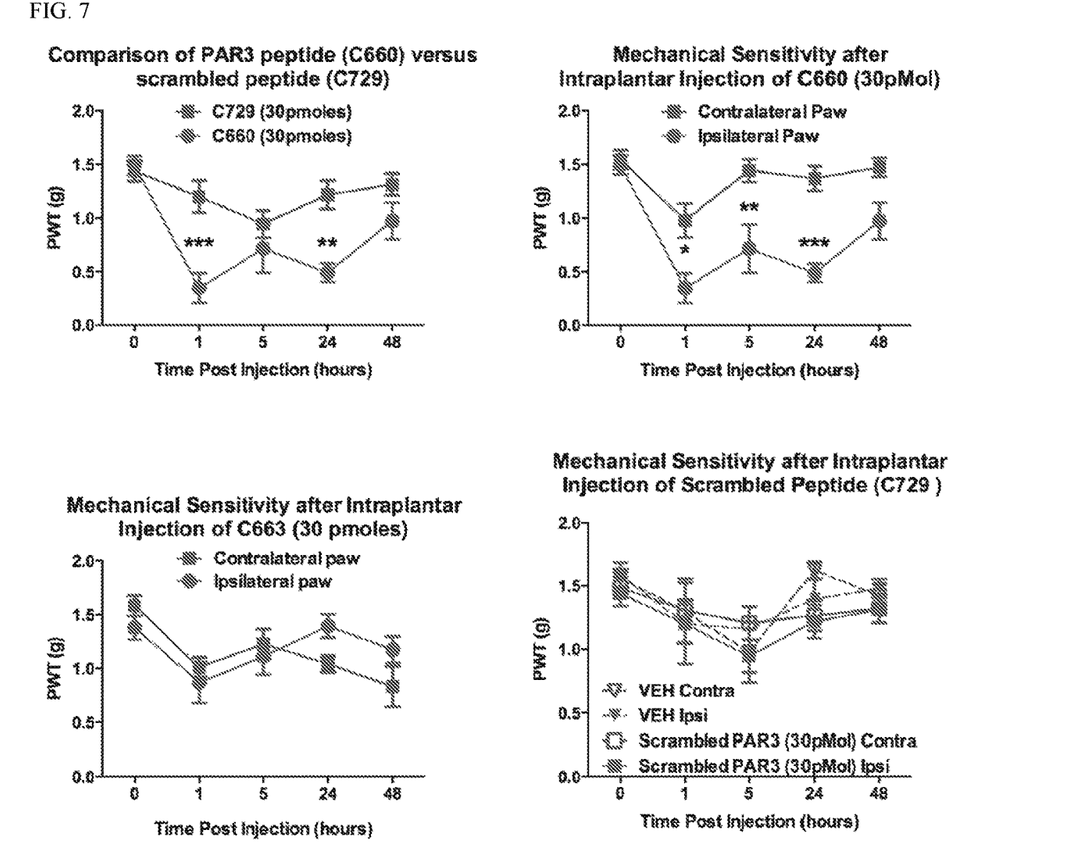
FIG. 7 shows that Compound 660 induces a pain response in mice.

Experiments conducted during the course of developing embodiments for the present invention identified the conspicuous DRG enriched gene F2RL2 which encodes $PAR_3$. Such experiments further demonstrated that several novel $PAR_3$ mimetic peptides robustly activated calcium signaling in trigeminal ganglion neurons and caused mechanical hypersensitivity after hindpaw injection in mice. Such experiments concluded $PAR_3$ to be a novel pain target.

Accordingly, the present invention relates to modulating compounds which function as activators and inhibitors of $PAR_3$ proteins. The invention further relates to methods of treating, ameliorating, or preventing disorders in a patient, such as those that are responsive to either $PAR_3$ activation or $PAR_3$ inhibition, comprising administering to a subject (e.g., a human patient) a composition comprising one or more of the $PAR_3$ modulating compounds of the invention and, potentially, additional agent(s). Such disorders include those characterized by aberrant $PAR_3$ activity (e.g., chronic pain).

The present invention is not limited to particular types or kinds of modulating compounds which function as activators and inhibitors of $PAR_3$ activity. In some embodiments, the modulating compounds include small molecule compounds and mimetic peptides.

In certain embodiments, the modulating compounds which function as activators and inhibitors of $PAR_3$ proteins are $PAR_3$ mimetic peptides. For example, in certain embodiments, the present invention provides compositions comprising a $PAR_3$ mimetic peptide. In some embodiments, the $PAR_3$ mimetic peptide is encompassed within Formula I:

[activating peptide sequence]-[linker moiety]-[cell-membrane anchoring moiety], including pharmaceutically acceptable salts, lipidated analogs, pegylated analogs, and/or prodrugs thereof.

Such $PAR_3$ mimetic peptides are not limited to a particular activating peptide sequence. In some embodiments, the peptide sequence comprises two or more contiguous amino acid residues. In some embodiments, the two or more contiguous amino acid residues render the resulting PAR3 mimetic peptide as a PAR3 activator and/or a PAR3 inhibitor. In some embodiments, the amino acid sequence is selected from the group consisting of TFRGAPPNSFEEF (SEQ ID NO: 1), GAPPNSFEEF (SEQ ID NO:2), TRFGAP (SEQ ID NO:3), and TFR.

Such $PAR_3$ mimetic peptides are not limited to a particular position for the activating peptide sequence. In some embodiments, the activating peptide sequence is positioned at the N-terminus of the $PAR_3$ mimetic peptide.

Such $PAR_3$ mimetic peptides are not limited to a particular linker moiety. In some embodiments, the linker moiety comprises a chemical moiety configured to bridge the activating peptide sequence and cell-membrane anchoring moiety. In some embodiments, the linker moiety comprises a chemical moiety selected from the group consisting of a substituted aliphatic chain, an unsubstituted aliphatic chain, substituted aromatic moiety, an unsubstituted aromatic moiety, a linear polymer, one or more polyethylene glycol (PEG) moieties, one or more 3,19-dioxo-2,8,11,14,21-pentaoxa-4,18-diazatricosan-23-oic acid residue derivative moieties, and/or any combination thereof. In some embodiments, the linker moiety comprises a polyethylene glycol (PEG) moiety. In some embodiments, the linker moiety comprises multimers of 3,19-dioxo-2,8,11,14,21-pentaoxa-4,18-diazatricosan-23-oic acid. In some embodiments, the linker moiety comprises a polyethylene glycol (PEG) moiety. In some embodiments, the linker moiety is a linear polymer comprising monomeric subunits. In some embodiments, the linear polymer comprises saccharide moieties, peptide moieties, lactone moieties, acrylate moieties, and/or synthetic polymer moieties. In some embodiments, the linear polymer comprises collagen-like polypeptides and/or synthetic surrogates of spider silk.

Such $PAR_3$ mimetic peptides are not limited to a particular cell-membrane anchoring moiety. In some embodiments, the cell-membrane anchoring moiety comprises a hydrophobic chemical moiety or a synthetic structure that forms a non-covalent binding interaction with a cell membrane.

Such $PAR_3$ mimetic peptides are not limited to a particular position for the cell-membrane anchoring moiety. In some embodiments, the cell-membrane anchoring moiety is positioned at the C-terminus of the $PAR_3$ mimetic peptide. In some embodiments, the cell-membrane anchoring moiety comprises a lipid moiety. In some embodiments, the cell-membrane anchoring moiety comprises a saturated or unsaturated hydrocarbon moiety. In some embodiments, the cell-membrane anchoring moiety is hexadecyl. In some embodiments, the cell-membrane anchoring moiety is a saturated $C_{12}$-$C_{20}$ alkyl residue. In some embodiments, the cell-membrane anchoring moiety is a cell-membrane homing structure. In some embodiments, the cell-membrane anchoring moiety is a cell-penetrating moiety. In some embodiments, the cell-membrane anchoring moiety is a transmembrane domain. Accordingly, the present invention relates to modulating compounds which function as activators and inhibitors of $PAR_3$ proteins. The invention further relates to methods of treating, ameliorating, or preventing disorders in a patient, such as those that are responsive to either $PAR_3$ activation or $PAR_3$ inhibition, comprising administering to a subject (e.g., a human patient) a composition comprising one or more of the $PAR_3$ mimetic peptides off the invention and, potentially, additional agent(s). Such disorders include those characterized by aberrant $PAR_3$ activity (e.g., inflammatory disorders).

In some embodiments, the length of the [linker moiety]-[cell-membrane anchoring moiety] is approximately 30-50 Angstroms.

In some embodiments, the $PAR_3$ mimetic peptide is configured to activate $PAR_3$ activity.

In some embodiments, the $PAR_3$ mimetic peptide is configured to antagonize $PAR_3$ activity.

Indeed, an important aspect of the present invention is that the compositions of the present invention are useful in treating conditions characterized with aberrant $PAR_3$ activity. For example, in some embodiments, compositions comprising $PAR_3$ modulating compounds (e.g., mimetic peptides) are used to treat acute pain and/or chronic pain related to $PAR_3$ activity. In some embodiments, the compositions and methods of the present invention are used to treat cells, tissues, organs, or pathological conditions and/or disease states in an animal (e.g., a mammalian patient including, but not limited to, humans and veterinary animals) having aberrant $PAR_3$ activity. In this regard, various diseases and pathologies are amenable to treatment or prophylaxis using the present methods and compositions.

Some embodiments of the present invention provide methods for administering an effective amount of a $PAR_3$ modulating compound (e.g., mimetic peptide) of the invention and at least one additional therapeutic agent (including, but not limited to, pain relieving agents) and/or therapeutic technique (e.g., surgical intervention, and/or radiotherapies).

In some embodiments, the pain relieving agents include, but are not limited to, analgesic drugs and respective antagonists. Examples of analgesic drugs include, but are not limited to, paracetamol and Non-steroidal anti-inflammatory drugs (NSAIDs), COX-2 inhibitors, opiates and morphonimimetics, and specific analgesic agents.

Examples of NSAIDs include, but are not limited to, salicylates (e.g., Acetylsalicylic acid (Aspirin), Aloxiprin, Benorylate/Benorilate, Choline magnesium salicylate, Diflunisal, Ethenzamide, Faislamine, Methyl salicylate, Magnesium salicylate, Salicyl salicylate, Salicylamide), arylalkanoic acids (e.g., Diclofenac, Aceclofenac, Acemetacin, Alclofenac, Bromfenac, Etodolac, Indometacin, Nabumetone, Oxametacin, Proglumetacin, Sulindac, Tolmetin), 2-arylpropionic acids (profens) (e.g., Ibuprofen, Alminoprofen, Benoxaprofen, Carprofen, Dexibuprofen, Dexketoprofen, Fenbufen, Fenoprofen, Flunoxaprofen, Flurbiprofen, Ibuproxam, Indoprofen, Ketoprofen, Ketorolac, Loxoprofen, Naproxen, Oxaprozin, Pirprofen, Suprofen, Tiaprofenic acid), N-arylanthranilic acids (fenamic acids) (e.g., Mefenamic acid, Flufenamic acid, Meclofenamic acid, Tolfenamic acid), pyrazolidine derivatives (e.g., Phenylbutazone, Ampyrone, Azapropazone, Clofezone, Kebuzone, Metamizole, Mofebutazone, Oxyphenbutazone, Phenazone, Sulfinpyrazone), oxicams (e.g., Piroxicam, Droxicam, Lornoxicam, Meloxicam, Tenoxicam), sulphonanilides (e.g., nimesulide), licofelone, and omega-3 fatty acids.

Examples of COX-2 inhibitors include, but are not limited to Celecoxib, Etoricoxib, Lumiracoxib, Parecoxib, Rofecoxib, Valdecoxib.

Examples of opiates include, but are not limited to, natural opiates (e.g., alkaloids contained in the resin of the opium poppy including morphine, codeine and thebaine), semi-synthetic opiates (e.g., created from the natural opioids, such as hydromorphone, hydrocodone, oxycodone, oxymorphone, desomorphine, diacetylmorphine (Heroin), nicomorphine, dipropanoylmorphine, diamorphine, benzylmorphine, Buprenorphine, Nalbuphine, Pentazocine, meperidine, diamorphine, and ethylmorphine), fully synthetic opioids (e.g., such as fentanyl, pethidine, Oxycodone, Oxymorphone, methadone, tramadol, Butorphanol, Levorphanol, and propoxyphene), and endogenous opioid peptides (e.g., produced naturally in the body, such as endorphins, enkephalins, dynorphins, and endomorphins).

Examples of analgesics include, but are not limited to, tricyclic antidepressants (e.g., amitriptyline, carbamazepine, gabapentin, and pregabalin), Tetrahydrocannabinol, ketamine, clonidine, $\alpha_2$-adrenoreceptor agonists, mexiletine, Orphenadrine, cyclobenzaprine, scopolamine, atropine, gabapentin, first-generation antidepressants and other drugs possessing anticholinergic and/or antispasmodic.

In some embodiments, pain relieving agents include anesthetic drugs. Examples of anesthetic drugs include, but are not limited to, local anesthetics (e.g., procaine, amethocaine, cocaine, lidocaine, prilocaine, bupivacaine, levobupivacaine, ropivacaine, dibucaine), inhaled anesthetics (e.g., Desflurane, Enflurane, Halothane, Isoflurane, Nitrous oxide, Sevoflurane, Xenon), intravenous anesthetics (e.g., Barbiturates (e.g., amobarbital (AMYTAL), pentobarbital (NEMBUTAL), secobarbital (SECONAL), Phenobarbital, Methohexital, Thiopental, Methylphenobarbital, Metharbital, Barbexaclone)), Benzodiazepines (e.g., alprazolam, bromazepam (LEXOTAN), chlordiazepoxide (LIBRIUM), Clobazam, Clonazepam, Clorazepate, Diazepam, Midazolam, Lorazepam, Nitrazepam, temazepam, nimetazepam, Estazolam, Flunitrazepam, oxazepam (SERAX), temazepam (Restoril, Normison, Planum, Tenox, and Temaze), Triazolam), Etomidate, Ketamine, and Propofol).

In some embodiments, pain relieving agents include anticonvulsant drugs. Examples of anticonvulsant drugs include, but are not limited to, aldehydes (e.g., paraldehyde), aromatic allylic alcohols (e.g., stiripentol), barbiturates (e.g., amobarbital (AMYTAL), pentobarbital (NEMBUTAL), secobarbital (SECONAL), Phenobarbital, Methohexital, Thiopental, Methylphenobarbital, Metharbital, Barbexaclone), benzodiazepines (e.g., alprazolam, bromazepam (LEXOTAN), chlordiazepoxide (LIBRIUM), Clobazam, Clonazepam, Clorazepate, Diazepam, Midazolam, Lorazepam, Nitrazepam, temazepam, nimetazepam, Estazolam, Flunitrazepam, oxazepam (SERAX), temazepam (Restoril, Normison, Planum, Tenox, and Temaze), Triazolam), bromides (e.g., potassium bromide), carbamates (e.g., felbamate), carboxamides (e.g., carbamazepine, oxcarbazepine), fatty acids (e.g., valproates (e.g., valproic acid, sodium valproate, and divalproex sodium), Vigabatrin, Progabide, Tiagabine), fructose derivatives (e.g., topiramate), gaba analogs (e.g., gabapentin, pregabalin), hydantoins (e.g., Ethotoin, Phenytoin, Mephenytoin, Fosphenytoin), Oxazolidinediones (e.g., paramethadione, trimethadione, ethadione), priopionates (e.g., primidone), pyrrolidines (e.g., brivaracetam, levetiracetam, seletracetam), succinimides (e.g., Ethosuximide, Phensuximide, Mesuximide), sulfonamides (e.g., Acetazolamide, Sulthiame, Methazolamide, Zonisamide), triazines (e.g., lamotrigine), ureas (e.g., pheneturide, phenacemide), and valproylamdies (amide derivatives of valproate) (e.g., valpromide, valnoctamide).

In some embodiments, pain relieving agents include muscle relaxant drugs. Examples of muscle relaxant drugs include, but are not limited to, depolarizing muscle relaxants (e.g., Succinylcholine), short acting non-depolarizing muscle relaxants (e.g., Mivacurium, Rapacuronium), intermediate acting non-depolarizing muscle relaxants (e.g., Atracurium, Cisatracurium, Rocuronium, Vecuronium), and long acting non-depolarizing muscle relaxants (e.g., Alcuronium, Doxacurium, Gallamine, Metocurine, Pancuronium, Pipecuronium, d-Tubocurarine).

In some embodiments, a $PAR_3$ modulating compound (e.g., mimetic peptide) of the invention and one or more pain relieving agents are administered to an animal (e.g., a human patient) under one or more of the following conditions: at different periodicities, at different durations, at different concentrations, by different administration routes, etc. In some embodiments, the $PAR_3$ modulating compound (e.g., mimetic peptide) is administered prior to the pain relieving agent, e.g., 0.5, 1, 2, 3, 4, 5, 10, 12, or 18 hours, 1, 2, 3, 4, 5, or 6 days, or 1, 2, 3, or 4 weeks prior to the pain relieving agent. In some embodiments, the $PAR_3$ modulating compound (e.g., mimetic peptide) is administered after pain relieving agent, e.g., 0.5, 1, 2, 3, 4, 5, 10, 12, or 18 hours, 1, 2, 3, 4, 5, or 6 days, or 1, 2, 3, or 4 weeks after the administration of the pain relieving agent. In some embodiments, the $PAR_3$ modulating compound (e.g., mimetic peptide) and the pain relieving agent are administered concurrently but on different schedules, e.g., the $PAR_3$ modulating compound (e.g., mimetic peptide) is administered daily while the pain relieving is administered once a week, once every two weeks, once every three weeks, or once every four weeks. In other embodiments, the $PAR_3$ modulating compound (e.g., mimetic peptide) is administered once a week while the pain relieving agent is administered daily, once a week, once every two weeks, once every three weeks, or once every four weeks.

Compositions within the scope of this invention include all compositions wherein the $PAR_3$ modulating compounds (e.g., mimetic peptides) of the present invention are contained in an amount which is effective to achieve its intended purpose. While individual needs vary, determination of optimal ranges of effective amounts of each component is within the skill of the art. Typically, the $PAR_3$ modulating compounds (e.g., mimetic peptides) may be administered to mammals, e.g. humans, orally at a dose of 0.0025 to 50 mg/kg, or an equivalent amount of the pharmaceutically acceptable salt thereof, per day of the body weight of the mammal being treated for disorders responsive to activation or inhibition of $PAR_3$ activity. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the $PAR_3$ modulating compound (e.g., mimetic peptide). The unit dose may be administered one or more times daily as one or more tablets or capsules each containing from about 0.1 to about 10 mg, conveniently about 0.25 to 50 mg of the $PAR_3$ modulating compound (e.g., mimetic peptide) or its solvates.

In a topical formulation, the $PAR_3$ modulating compound (e.g., mimetic peptide) may be present at a concentration of about 0.01 to 100 mg per gram of carrier. In a one embodiment, the $PAR_3$ modulating compound (e.g., mimetic peptide) is present at a concentration of about 0.07-1.0 mg/ml, for example, about 0.1-0.5 mg/ml, and in one embodiment, about 0.4 mg/ml.

In addition to administering the $PAR_3$ modulating compound (e.g., mimetic peptide) as a raw chemical, the $PAR_3$ modulating compounds (e.g., mimetic peptides) of the invention may be administered as part of a pharmaceutical preparation containing suitable pharmaceutically acceptable carriers comprising excipients and auxiliaries which facilitate processing of the $PAR_3$ modulating compounds into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active mimetic peptide(s), together with the excipient.

The pharmaceutical compositions of the invention may be administered to any patient which may experience the beneficial effects of the $PAR_3$ modulating compounds (e.g., mimetic peptides) of the invention. Foremost among such patients are mammals, e.g., humans, although the invention is not intended to be so limited. Other patients include veterinary animals (cows, sheep, pigs, horses, dogs, cats and the like).

The $PAR_3$ modulating compounds (e.g., mimetic peptides) and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active mimetic peptides with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active mimetic peptide doses.

Other pharmaceutical preparations which can be used orally include push-fit capsules made of gelatin, as well as soft, sealed capsules made of gelatin and a plasticizer such as glycerol or sorbitol. The push-fit capsules can contain the active mimetic peptides in the form of granules which may be mixed with fillers such as lactose, binders such as starches, and/or lubricants such as talc or magnesium stearate and, optionally, stabilizers. In soft capsules, the active mimetic peptides are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active mimetic peptides with a suppository base. Suitable suppository bases are, for example, natural or synthetic triglycerides, or paraffin hydrocarbons. In addition, it is also possible to use gelatin rectal capsules which consist of a combination of the active mimetic peptides with a base. Possible base materials include, for example, liquid triglycerides, polyethylene glycols, or paraffin hydrocarbons.

Suitable formulations for parenteral administration include aqueous solutions of the active mimetic peptides in water-soluble form, for example, water-soluble salts and alkaline solutions. In addition, suspensions of the active mimetic peptides as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

EXPERIMENTAL

Example I

The dorsal root ganglion (DRG) contains sensory neurons that innervate the surface of the body and many visceral organs. Included amongst these neurons are nociceptors, specialized neurons that detect damaging or potentially damaging stimuli, which are required for the detection of acute pain and play a key role in the development and maintenance of chronic pain states. RNA-seq has recently been used to elucidate the transcriptome of this tissue in mouse and rat but the transcriptome of human DRG has not been explored.

Fresh, lumbar DRG tissue was obtained from female human donors and performed 75 bp paired-end polyA+ RNA-sequencing on the Illumina platform. The sequenced fragments were mapped to the Gencode v14 reference transcriptome/hg19 reference genome to yield 80M mapped fragments, and relative transcript abundance in TPMs (Transcripts per Million reads) was quantified using the Tophat-Cufflinks toolkit. A RNA-seq dataset was compared to publicly available mouse DRG RNA-seq data and performed integrative analysis with RNA-seq data from several tissues associated with drug side effects (e.g. heart, small intestines, whole brain) to perform an unbiased search for conserved gene expression in DRG across both species. It was found that there is broad conservation of known DRG and/or nociceptor enriched genes (e.g. P2XR3, SCN10A, SCN11A, NTRK1, MRGPRD) across mouse and human DRGs. Information theory approaches were used to identify tissue-specific genes in human and mouse DRG compared to 13 other tissues in human and mouse. Strong correlation of expression was found across tissues between species for a few hundred DRG-enriched transcripts, including known genes enriched in the DRG and previously unidentified ones.

A conspicuous DRG enriched gene is F2RL2 which encodes $PAR_3$ was identified. $PAR_3$ expression in DRG is amongst the highest for all G protein coupled receptors (GPCRs) in human and mouse and mapping of existing cellular expression databases suggests neuronal expression in a population of nociceptors.

To test the potential role of $PAR_3$ in pain, novel ligands for this receptor were developed using a synthetic tethered ligand discovery platform for PARs. Such novel ligands were shown to robustly activate calcium signaling in trigeminal ganglion neurons and cause mechanical hypersensitivity after hindpaw injection in mice but are devoid of activity at $PAR_2$.

It was concluded that GPCR expression in human and mouse DRG is similar with some notable differences mostly in terms of magnitude of expression.

It was concluded that of the PAR receptor family, $PAR_3$ is most highly expressed in human and mouse DRG and is high in DRG compared to almost all other tissues.

It was concluded that a $PAR_3$-derived synthetic tethered ligand robustly activates Calcium signaling in mouse TG neurons and induces mechanical hypersensitivity in vivo consistent with a role for $PAR_3$ (f2rl2 gene) in nociceptive plasticity.

It was concluded that such experiments reveal $PAR_3$ as a novel pain target.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A composition comprising a protease activator receptor type-3 (PAR$_3$) mimetic peptide consisting of Formula I: [activating peptide sequence]-[linker moiety]-[cell-membrane anchoring moiety] (Formula I), or pharmaceutically acceptable salts, lipidated analogs, pegylated analogs, and/or prodrugs thereof;

wherein the activating peptide sequence consists of the amino acid sequence selected from TFRGAPPNSFEEF (SEQ ID NO:1) and GAPPNSFEEF (SEQ ID NO:2);

wherein the linker moiety consists of a polyethylene glycol (PEG) moiety and/or multimers of 3,19-dioxo-2,8,11,14,21-pentaoxa-4,18-diazatricosan-23-oic acid;

wherein the cell-membrane anchoring moiety comprises a hydrophobic chemical moiety or a synthetic structure that forms a non-covalent binding interaction with a cell membrane; and wherein the PAR$_3$ mimetic peptide is configured to activate PAR$_3$ biological activity.

2. The composition of claim 1, wherein the cell-membrane anchoring moiety comprises at least one of a lipid moiety, multimers of 3,19-dioxo-2,8,11,14,21-pentaoxa-4,18-diazatricosan-23-oic acid, a saturated and unsaturated $C_{12}$-$C_{20}$ residues, hexadecyl, a cell-membrane homing structure, a cell-penetrating moiety, or a transmembrane domain.

3. A method for increasing the activity of PAR$_3$ in a subject in need thereof, comprising administering to the subject a composition as recited in claim 1.

4. The method of claim 3, wherein the subject is a human subject.

5. The method of claim 3, wherein the subject has or is at risk for developing chronic pain related to PARS activity.

6. The method of claim 5, further comprising administering to the subject one or more pain relieving agents.

7. A pharmaceutical composition comprising a composition as recited in claim 1 and a pharmaceutically acceptable carrier.

8. A kit comprising (1) a pharmaceutical composition as recited in claim 7, (2) a container, pack, or dispenser, and (3) instructions for administration.

* * * * *

UNITED STATES PATENT AND TRADEMARK OFFICE
CERTIFICATE OF CORRECTION

PATENT NO. : 11,306,130 B2
APPLICATION NO. : 16/090526
DATED : April 19, 2022
INVENTOR(S) : Josef Vagner et al.

It is certified that error appears in the above-identified patent and that said Letters Patent is hereby corrected as shown below:

In the Claims

Column 14, Claim 3, Line 65 reads:
A method for increasing the activity of PARS in a Whereas it should read:
A method for increasing the activity of $PAR_3$ in a Column 15, Claim 5, Line 4 reads:
risk for developing chronic pain related to PARS activity.

Whereas it should read:
risk for developing chronic pain related to $PAR_3$ activity.

Signed and Sealed this
Twentieth Day of September, 2022

Katherine Kelly Vidal
*Director of the United States Patent and Trademark Office*

SEQUENCE LISTING

```
<160> NUMBER OF SEQ ID NOS: 8

<210> SEQ ID NO 1
<211> LENGTH: 13
<212> TYPE: PRT
<213> ORGANISM: Artificial Sequence
<220> FEATURE:
<223> OTHER INFORMATION: synthetic

<400> SEQUENCE: 1

Thr Phe Arg Gly Ala Pro Pro Asn Ser Phe Glu Glu Phe
1               5                   10

<210> SEQ ID NO 2
<211> LENGTH: 10
<212> TYPE: PRT
<213> ORGANISM: Artificial Sequence
<220> FEATURE:
<223> OTHER INFORMATION: synthetic

<400> SEQUENCE: 2

Gly Ala Pro Pro Asn Ser Phe Glu Glu Phe
1               5                   10

<210> SEQ ID NO 3
<211> LENGTH: 6
<212> TYPE: PRT
<213> ORGANISM: Artificial Sequence
<220> FEATURE:
<223> OTHER INFORMATION: synthetic

<400> SEQUENCE: 3

Thr Arg Phe Gly Ala Pro
1               5

<210> SEQ ID NO 4
<211> LENGTH: 13
<212> TYPE: PRT
<213> ORGANISM: Artificial Sequence
```

```
<220> FEATURE:
<223> OTHER INFORMATION: synthetic

<400> SEQUENCE: 4

Pro Gly Thr Glu Phe Asn Phe Ala Arg Glu Ser Phe Pro
1               5                   10

<210> SEQ ID NO 5
<211> LENGTH: 14
<212> TYPE: PRT
<213> ORGANISM: Artificial Sequence
<220> FEATURE:
<223> OTHER INFORMATION: synthetic

<400> SEQUENCE: 5

Arg Thr Phe Arg Gly Ala Pro Pro Asn Ser Phe Glu Glu Phe
1               5                   10

<210> SEQ ID NO 6
<211> LENGTH: 4
<212> TYPE: PRT
<213> ORGANISM: Artificial Sequence
<220> FEATURE:
<223> OTHER INFORMATION: synthetic

<400> SEQUENCE: 6

Phe Glu Glu Phe
1

<210> SEQ ID NO 7
<211> LENGTH: 6
<212> TYPE: PRT
<213> ORGANISM: Artificial Sequence
<220> FEATURE:
<223> OTHER INFORMATION: synthetic

<400> SEQUENCE: 7

Asn Ser Phe Glu Glu Phe
1               5

<210> SEQ ID NO 8
<211> LENGTH: 6
<212> TYPE: PRT
<213> ORGANISM: Artificial sequence
<220> FEATURE:
<223> OTHER INFORMATION: synthetic

<400> SEQUENCE: 8

Thr Phe Arg Gly Ala Pro
1               5
```